United States Patent [19]

Nipp

[11] Patent Number: 4,848,587

[45] Date of Patent: Jul. 18, 1989

[54] CONTAINER FOR STORING MATERIALS FOR USE BY DIABETICS

[76] Inventor: Kenneth Nipp, 318 S. Crimson, No. 35, Mesa, Ariz. 85208

[21] Appl. No.: 46,923

[22] Filed: May 7, 1987

[51] Int. Cl.$^4$ ............................................. A65D 69/00
[52] U.S. Cl. ..................................... 206/571; 206/459; 206/534; 206/538; 220/22; 220/334
[58] Field of Search ............... 206/570, 571, 534, 538, 206/459; 220/334, 335, 22

[56] References Cited

U.S. PATENT DOCUMENTS

| | | | |
|---|---|---|---|
| 1,625,547 | 4/1927 | Kessler | 206/570 |
| 2,062,973 | 12/1936 | Gluckstein | 206/570 |
| 3,338,389 | 8/1967 | Sellen et al. | 220/22 |
| 3,491,909 | 1/1970 | Ikelheimer | 220/22 |
| 4,038,937 | 8/1977 | Moe | 206/538 |
| 4,250,998 | 2/1981 | Taylor | 206/571 |
| 4,325,595 | 4/1982 | Solomon | 220/335 |
| 4,429,793 | 2/1984 | Ehmann | 206/571 |
| 4,446,966 | 5/1984 | Moloney | 220/22 |

FOREIGN PATENT DOCUMENTS 48867  3/1982  European Pat. Off. ............ 206/570

*Primary Examiner*—Stephen Marcus

*Attorney, Agent, or Firm*—Harry M. Weiss

[57] ABSTRACT

An improved container for storing medical supplies most commonly used by diabetics is described. Five compartments are provided arranged within an openable rectangular box with substantially no waste space. A first longitudinal compartment runs the entire length of the box for receiving packaged sterile syringes. A second longitudinal compartment parallel to the first runs part way down the length of the box for storing sterilizing swabs or wipes in sealed packages. Between this second compartment and the far end of the box is a third smaller longitudinal compartment for holding glucose test tapes, and in the remaining space are two serially arranged square or round compartments for receiving upright insulin bottles or the like. The rear wall of the box and the partitions separating the compartments are lower than the other sides of the box to make removal of the contents easier. An optional clip is provided inside the lid for retaining a prefilled syringe for emergency use. The hinge between the lid and the compartmented box is preferably arranged to hold the lid in a partially upright position when open with its center of gravity behind the hinge points so that gravity prevents it from falling shut.

2 Claims, 1 Drawing Sheet

CONTAINER FOR STORING MATERIALS FOR USE BY DIABETICS

BACKGROUND OF THE INVENTION

1. Field of the Invention

This invention relates to a container for transporting and storing medical supplies and, in particular, a compartmented box for storing and transporting medical supplies used by diabetics.

2. Background Art

Diabetes is a medical condition which afflicts many people and unless controlled can be life threatening. A principal means of controlling diabetes is insulin therapy wherein the diabetic receives insulin injections one or more times each day. It is common for many insulin sustained diabetics to administer these injections themselves.

The frequency and amount of insulin injection which may be needed usually depends upon the diabetic's glucose level. Today this can be measured very simply by means of a specially treated test tape which is immersed in a urine sample. The test tape changes color to indicate the glucose level.

To accomplish such insulin treatment, what is needed is a ready supply of the test tape, a bottle or vial of insulin, a means for sterilizing the skin and the seal on the bottle or vial, and one or more hypodermic syringes for extracting the insulin from the storage bottle or vial and injecting it beneath the patient's skin. Sometimes, several types of insulin are needed if the patient uses more than one type.

However, merely possessing the necessary materials is often not enough for safe reliable treatment. This is because on some occasions the diabetic's need for insulin may change so rapidly that unless the diabetic makes the injection quickly, he or she may become incapacitated and have great difficulty in making the proper injection or be unable to make it at all. Therefore there is a continuing need for containers particularly adapted for the storage of such diabetic treatment supplies in a way that they may be accessed quickly and without confusion even in the dark and/or during the onset of diabetic attack. Moreover, the container should be capable of holding several day's supply and be readily transportable.

A number of containers are known in the prior art for holding hypodermic synringes and for holding various diabetic treatment supplies. Examples of such units are described in U.S. Pat. Nos. 195,947, 1,625,035, 2,077,240, 2,740,516, 3,058,584, 4,429,793, 4,446,970, and 4,523,679 which are incorporated herein by reference. However, these prior art containers suffer from a number of disadvantages, such as for example, being poorly arranged to receive the most modern forms of the various treatment elements, and/or failing to provide storage for all the elements needed, and/or failing to provide storage which can be unequivocally accessed even in the dark, and/or failing to provide or facilitate a quick-response capability for those instances when extremely rapid injection is needed.

Accordingly, it is an objective of the present invention to provide an improved container for holding diabetic treatment supplies which is compact and provides for storage of the treatment components in particular and well identified locations.

It is a further objective of the present invention to provide an improved container for holding diabetic treatment supplies which is particularly adapted to the most modern forms of such supplies and which is compact and without waste space.

It is an additional objective of the present invention to provide an improved container for holding diabetic treatment supplies wherein there are separate compartments for the individual treatment elements which have distinct sizes and shapes which can be identified by touch alone.

It is a further objective of the present invention to provide an improved container for holding diabetic treatment supplies which, in addition to holding routinely used supplies, also is adapted to hold in a prominent and easily located position, an emergency prefilled syringe ready for use with minimum delay.

SUMMARY OF THE INVENTION

These and other advantages and objectives are achieved by the present invention by providing a medical storage container for diabetics comprising a box with a bottom portion and lid portion, wherein the bottom portion is deeper than the lid portion, wherein the bottom portion has a first compartment of a length and breadth for receiving in a longitudinal orientation with respect to one dimension of the box, sterilized packaged hypodermic syringes, a second compartment of a length and breadth for receiving individually packaged antiseptic sterilization means, a third compartment of a length and breadth for receiving glucose test tape, and one of more further compartments of a cross-section for receiving one or more upright insulin bottles, one bottle per compartment, and further, an optional clip means attached to the underside of said lid portion for removably retaining a precharged insulin syringe.

It is desirable that the lid portion be hinged to the bottom portion, preferably using two hinge means which pivot on opposite ends of the bottom portion on pivot points which are inset from the rear side of the box and which lie below the upper edge of the bottom portion. The hinge length and pivot location should be such that when the lid is rotated on the hinges into the open position, the lower rear edge of the top portion comes to rest against the rear side of the bottom portion and the lid portion stands partially upright, slightly beyond the vertical with respect to the rear side of the bottom portion and with its center of gravity on the rearward side of the pivot points so that it remains in the open position by gravity.

It is also desirable that the height of the partitions of the bottom portion which form the various compartments be less than the height of the sides, and that the heights of the sides and ends vary so that they are lower in the location of the insulin bottles. This arrangement permits the bottles to be readily grasped and removed from the box. With the exception of the two insulin compartments, the other compartments may be distinguished in the dark or by a sight impaired diabetic by having a different shape which is characteristic of the objects being stored. The two insulin compartments may have the same or different shape from each other. Where the same shape is used, the portions of the partition immediatey adjacent the compartments for storing the insulin bottles may be notched or have other integral touch differentiation so that each bottle compartment may be distinguished in the dark. It is convenient that the depth of the top portion vary so as to be complementary to the bottom portion so that when the lid is closed, the box has a substantially uniform height.

A further understanding of the invention will be obtained by consideration of the figures and description which follow.

DETAILED DESCRIPTION OF THE DRAWINGS

Figure 1:
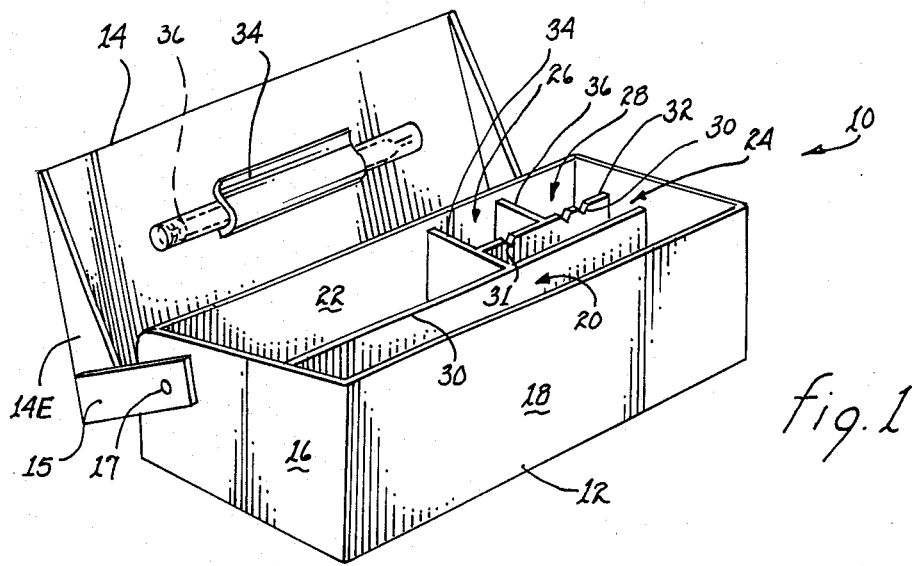
FIG. 1 is a perspective view of the diabetic supply box of the present invention with the lid in the open position and according to a first embodiment.
Figure 2:
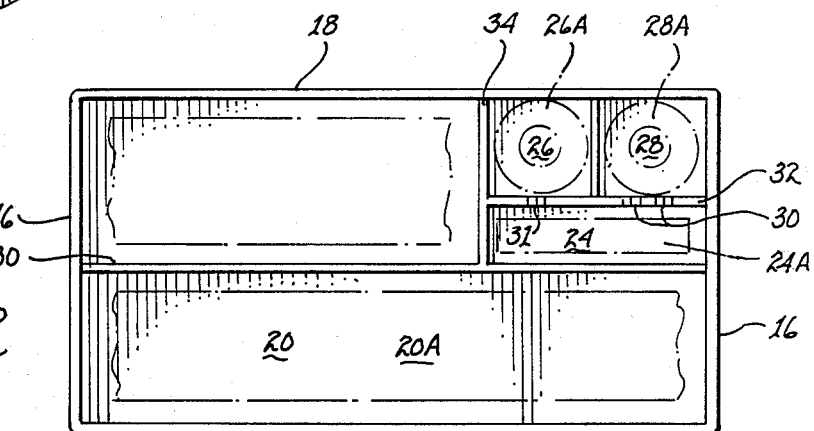
FIG. 2 is a top view of the box of FIG. 1 with the lid removed.
Figure 3:
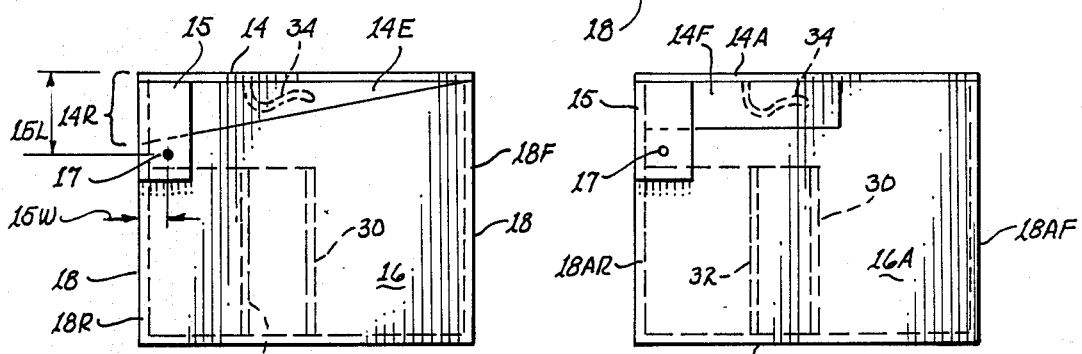
FIG. 3 is an end view of the box of FIG. 1 with the lid closed.
Figure 4:
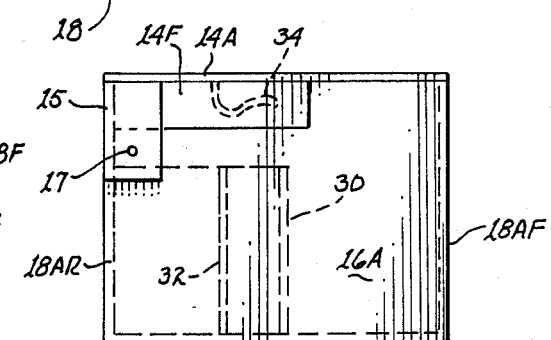
FIG. 4 is an end view similar to FIG. 3 but according to a further embodiment.
Figure 5:
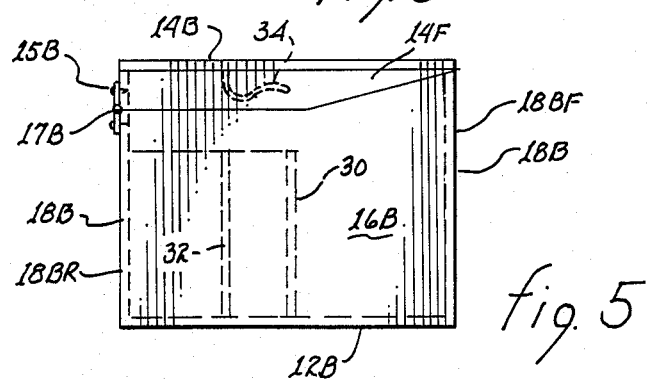
FIG. 5 is an end view similar to FIG. 3 but according to a still further embodiment.

FIG. 1 is a simplified perspective view of diabetic box 10 according to a preferred embodiment of the present invention. FIG. 2 is a top view with the lid removed and FIG. 3 is an end view of the box of FIG. 1 with the lid in place. FIGS. 4 and 5 show end views of further embodiments. Understanding of the features and construction of box 10 is best obtained by considering FIGS. 1–5 together.

Box 10 comprises bottom portion 12 having ends 16 and sides 18, top portion 14 having ends 14E, hinge means 15 with pivot pin means 17, principal longitudinal partition 30, partial lateral partition 34, smaller longitudinal partition 32, and smaller lateral partition 36. Together with ends 16 and sides 18, these partitions form first compartment 20 for receiving packaged sterile syringes 20A, second compartment 22 for receiving means 22A for sterilizing the user's skin and/or the insulin bottle seals, as for example, pre-packages alcohol pads or swabs, third compartment 24 for receiving glucose test tapes 24A, and fourth and fifth compartments 26, 28 for receiving insulin bottles 26A, 28A. Longitudinal partitions 30, 32 are desirably substantially parallel to sides 18 and lateral partitions 34, 36 are desirably substantially parallel to ends 16. Partition 36 is conveniently located substantially at the mid-point of partition 32.

Syringes 20A are typically sealed in a sterile wrapping and are disposable. Certain standard size syringes are preferred for diabetic use and compartment 20 is desirably sized to accept such pre-packaged syringes. Typical internal dimensions for compartment 20 are about 5¾ths inches long by about 1¼th inches wide, but other sizes can be used provided that they accommodate the desired syringes. The long comparatively narrow shape of compartment 20 provides a natural touch-only recognition of this compartment as containing the syringes. It is the longest compartment in the box.

Sterilization pads or swabs 22A are generally shorter and wider than the syringes, so compartment 22 has a corresponding shape so as to also provide a natural touch-only recognition of the location of the sterilization pads. Typical internal dimensions for compartment 22 are about 3¾th inch long by about 1½ inch wide, but other dimensions adapted to fit the dimensions of other sterilization swabs or pads can also be used, consistent with the requirement that each compartment fit together compactly with the other compartments within box 10 without significant waste space.

Compartment 24 is adapted to receive test tapes 24A and is typically about 2 inches long by about ½ inch wide inside. Compartments 26 and 28 for insulin or other bottles 26A, 28A are typically about ¾ inch to 1 inch square inside to accommodate the standard dimensions of upright insulin bottles or bottles for other injectable medication. While square compartments are useful for the insulin bottles and a square external shape for the insulin compartments is most convenient for integration with the other compartments, the internal shapes of the two insulin compartments need not be square. Other internal shapes can also be used, including different shapes for each bottle compartment provided that they are such that the insulin bottles fit snugly therein.

Overall outside dimensions of box 10 are conveniently about 6 inches long by about 3¼ inch wide by about 2½ inch high. However, this is merely to illustrate convenient proportions and sizes for holding modern diabetic treatment supplies and larger and smaller boxes consistent with the size of the supplies desired to be stored therein may also be used.

Lid portion 14 of box 10 rotates on hinge means 15 on pivots 17 so that when fully opened lid portion 14 rests against the rear side of box 10 in a partially upright position, preferably just past the vertical, so that lid portion 14 is prevented from falling shut by gravity. In this position the lid portion 14 makes an interior angle of less than ninety degrees with respect to rear side 18R of bottom portion 12.

Portion 14R of the rear side of box 10 is part of movable lid portion 14, rather than part of rear side 18R of bottom portion 12. The vertical dimension of portion of 14R is adjusted in relation to hinge pivot location distances 15L and 15W so that portion 14R swings in an arc until its lower rear edge rests against side 18R when lid portion 14 is open. Hinge points 17 are located a predetermined vertical distance between the upper and lower edges of bottom portion 12, preferably closer to the upper edge and inset (frontward) from rear side 18R by distance 15W. The further that pivot points 17 are below the upper rear edge of bottom portion 12, the greater the arc through which lid portion 14 will travel between its open and closed position. By arranging to have the amount of rotation of hinge means 15 and lid portion 14 exceed ninety degrees, then when rear lower edge of lid portion 14 comes to rest against rear side 18R when lid portion 14 is fully open, the center of gravity of lid portion 14 will be behind pivot points 17 so that gravity prevents lid portion 14 from falling shut. Between the closed and open positions of lid portion 14, hinge means 15 and lid portion 14 desirably rotate through an angle exceeding ninety degrees but less than one hundred and eighty degrees.

This partially upright stable open position of lid portion 14 is especially convenient since it places optional prefilled emergency syringe 36 held to lid 14 by clip 34 in an easily accessible location. The user does not have to hunt inside box 10 to find the emergency syringe. Merely raising lid 14 brings the emergency syringe immediately to hand. This is a very useful feature when an emergency injection is required.

As can be seen in FIG. 3, ends 16 of bottom portion 12 of box 10 shown in FIG. 1 are not as tall toward the rear hinge side of box 10. This facilitates removal of bottles 26A, 28A which stand upright in compartments 26, 28 since side 18R and low partitions 32, 34, 36 do not interfere. The provision of at least two bottle compartments is particularly desirable since many diabetics use two different kinds of insulin and want to have both readily at hand.

Where insulin bottle compartments 26, 28 have the same shape, then it is useful to provide notches 30, 31 or other integral touch differentiation markers in partition 32 or on the interior surface of side 18R adjacent each compartment. This permits the user to identify a particular compartment and bottle by touch only. This is particularly useful for sight impaired diabetics or during darkness. Any tactile coding means may be used, but notches or bumps on partition 32 are particularly convenient.

FIGS. 1-3 illustrate the embodiment wherein ends 14E, 16 of top portion 14 and bottom portion 12 taper uniformly from front to rear of box 10, i.e., from front side 18F to rear hinge side 18R so that rear side 18R is shorter than front side 18F. The shapes of the lid or top of the box and the bottom of the box are desirably complimentary so that when box 10 is closed it is overall approximately of uniform height and there are no significant gaps in the sides or ends.

FIG. 4 illustrates another embodiment in which box 10 has substantially the same interior arrangement of partitions and compartments, but ends 14F and 16A of top 14A and bottom 12A have a complementary notched shape, but still with rear side 18AR shorter than front side 18AF. The hinge arrangement in FIG. 4 is similar to that shown in FIGS. 1-3 so that top 14 has the same tilt-up and stop motion when opened.

FIG. 5 illustrates a further embodiment in which ends 14F and 16B have a complementary joint comprising a substantially horizontal portion followed by an angled portion so that rear side 18BR continues to be shorter than front side 18BF and the overall height is still uniform. FIG. 5 also illustrates a further embodiment of the hinge between top 14B and bottom 12B. In this case, a hinge is employed which has a pivot substantially in line with the joint between top 14B and bottom 12B rather than being off-set as in FIGS. 1-4. This permits top 14B to open to a wider angle. Hinge 15B with pivot 17B may be of a conventional articulating piano type hinge or a thin flexible plastic membrane type hinge. Either will serve.

Plastic is a suitable material for box 10. Box 10 may be molded or assembled. Where the box is molded, the plastic membrane hinge may be molded at the same time as the box.

It will be readily apparent based on the foregoing description that the box of the present invention provides tactily identifiable storage compartments adapted to optimally accommodate modern diabetic treatment supplies in an especially convenient way. The shape of each compartment corresponds in a natural way with the shape of the objects being stored therein, yet the whole is fitted into an overall simple rectangular shape that is easy to hold, store, pack, and use, and yet which has little if any waste space. Further, the lid is optionally adapted to receive a prefilled emergency syringe which can be quickly and easily located in an emergency without searching through the box when very rapid injection of insulin is needed. The tapering of the ends of the bottom portion of the box from front to back makes it easy to remove the insulin bottles which stand up in compartments adjacent to the rear wall of the box. While the bottle compartments are conveniently square for accommodating a round bottle, they could also be round or have other regular interior geometric shape into which a circular object will easily fit, and each compartment can have a different internal shape. It is intended to include all such variations as fall within the scope of the claims that follow.

I claim:

1. A container for storing medical supplies for diabetics comprising:

a box having a lower bottom portion and a mating upper lid portion, wherein said lower portion comprises first and second ends and front and rear sides and a bottom, wherein said sides are longer than said ends, and wherein said height of said front side is greater than said height of said rear side;

a first longitudinal partition within said box extending between said ends and to said bottom and substantially parallel to said front side and having a height less than said height of said front side, wherein said first partition together with portions of said front side, said ends, and said bottom form a first compartment extending between said ends, said first compartment having a length and width sufficient to store packaged sterile syringes;

a second transverse partition extending from said first partition to said rear side and said bottom and having at least one face substantially parallel to said first end and having a height less than said rear side, and wherein said second partition together with portions of said first partition, said first end, said rear side, and said bottom form a second compartment extending from said first end to said second partition, said second compartment having a length and width sufficient to store pre-packaged alcohol pads or swabs;

a third longitudinal partition extending from said second partition to said second end and to said bottom and having a height less than said rear side, and wherein said third partition together with portions of said second partition, said second end, said bottom, and said first partition form a third compartment extending from said third partition to said second end, said third compartment having a length and width sufficient to store glucose test tapes;

a fourth transverse partition extending from said third partition to said rear side and to said bottom and having a height less than said rear side, and wherein said fourth partition together with portions of said third partition, said bottom, said second partition, and said rear side form a fourth compartment, and wherein said fourth partition together with portions of said third partition, said bottom, said second end, and said rear side form a fifth compartment, said fourth and said fifth compartment being substantially equal in size and each having a width and length sufficient to store a small insulin bottle; and hinge means pivoted on said first and second ends and fixed to said top portion for allowing said portion to swing up and away from said bottom portion.

2. A diabetic supply container comprising:

a closeable box split into a top portion and bottom portion by a joint which is at a first height from the bottom of said box adjacent a first side and at a second smaller height from the bottom of said box adjacent a second opposite side; and open compartments disposed within said bottom portion of said box and comprising a first longitudinal compartment extending from end to end of said box, said first longitudinal compartment having a length and width sufficient to store packaged sterile syringes, a second parallel longitudinal compartment adjacent said first compartment and extending from a first end of said box part way toward a second end of said box, said second parallel longitudinal compartment having a length and width sufficient to store pre-packaged alcohol pads or swabs, a third longitudinal compartment parallel and adjacent to said first compartment and extending from said second compartment to said second end, said third longitudinal compartment having a length and width sufficient to store glucose test tapes, and fourth and fifth compartments extending serially from said second compartment to said second end adjacent said third compartment, said fourth and said fifth compartment being substantially equal in size and each having a width and length sufficient to store a small insulin bottle, wherein said first, second, and third longitudinal compartments have respectively diminishing lengths and wherein said fourth and fifth compartments have internal lateral shape for snugly receiving upright cylindrical bottles, and wherein said compartments are separated by partitions.

* * * * *